United States Patent [19]

Remy

[11] 4,062,891
[45] Dec. 13, 1977

[54] N-FORMYL-2,3,5,6-DIBENZOBICYCLO[5.1.0-]OCTAN-4-METHYLAMINE

[75] Inventor: David C. Remy, North Wales, Pa.

[73] Assignee: Merck & Co., Inc., Rahway, N.J.

[21] Appl. No.: 728,677

[22] Filed: Oct. 1, 1976

Related U.S. Application Data

[60] Division of Ser. No. 309,832, Nov. 27, 1972, abandoned, which is a continuation-in-part of Ser. No. 827,038, May 22, 1969, abandoned, which is a continuation-in-part of Ser. No. 663,930, Aug. 24, 1967, abandoned.

[51] Int. Cl.$^2$ .............................................. C07C 103/37
[52] U.S. Cl. ............................. 260/562 P; 260/465 R; 260/562 R; 260/570.9; 424/330
[58] Field of Search .......................... 260/562 P, 562 R

[56] References Cited

U.S. PATENT DOCUMENTS

| | | | |
|---|---|---|---|
| 3,423,461 | 1/1969 | Kaiser et al. | 260/562 R |
| 3,574,199 | 4/1971 | Coyne et al. | 260/240 TC |

Primary Examiner—Arthur P. Demers
Attorney, Agent, or Firm—Daniel T. Szura; Thomas E. Arther; Harry E. Westlake, Jr.

[57] ABSTRACT

The new 4-aminomethyldibenzobicyclo[5.1.0]octane compounds of the present invention are prepared from the corresponding 4-halo compounds by reaction with a metal cyanide to produce the corresponding 4-cyano compound, which is reduced with an alkali metal aluminum hydride to produce the desired 4-aminomethyl compound. These new aminomethyldibenzobicyclo[5.1.0]octane compounds are converted to the corresponding secondary and tertiary amino derivatives.

These new compounds are useful as antiarrhythmic agents and can be used to overcome cardiac irregularities.

2 Claims, No Drawings

N-FORMYL-2,3,5,6-DIBENZOBICYCLO[5.1.0]OC-TAN-4-METHYLAMINE

This is a division of copending U.S. application Ser. No. 309,832, filed Nov. 27, 1972, now abandoned which in turn is a continuation-in-part of U.S. application Ser. No. 827,038, filed May 22, 1969, now abandoned, which in turn is a continuation-in-part of U.S. application Ser. No. 663,930, filed Aug. 24, 1967, now abandoned.

This invention relates to novel dibenzobicyclo-[5.1.0]octane compounds and processes of preparing the same.

More particularly, the invention is concerned with novel dibenzobicyclo[5.1.0]octane compounds having a 4-aminomethyl substituent, acid addition salts thereof, novel processes for the preparation of such compounds and to novel intermediates found to be useful in the preparation of such compounds.

The new 4-aminomethyldibenzobicyclo[5.1.0]octane compounds as well as the secondary and tertiary amino derivatives thereof, have the following general formula:

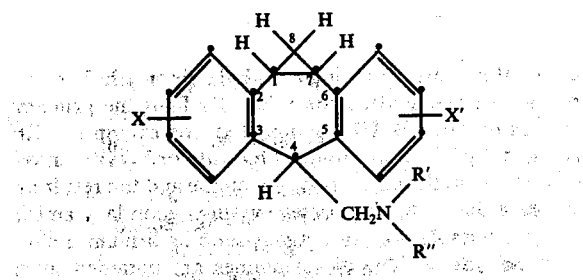

wherein X and X' are similar or dissimilar and are selected from hydrogen, lower alkyl (1–4 carbon atoms), a phenyl or substituted phenyl radical, an amino, an alkylamino having up to 4 carbon atoms, a dialkylamino having up to 4 carbon atoms, an alkylsulfonyl group having up to 4 carbon atoms, hydroxyl, alkoxyl having up to 4 carbon atoms, mercapto, an alkylmercapto having up to 4 carbon atoms, sulfamoyl, an alkylsulfamoyl having up to 4 carbon atoms, and R' and R" are each hydrogen or alkyl, or together form with the nitrogen atom attached thereto a heterocyclic ring having from 5 to 7 members which may include at least one additional hetero atom selected from nitrogen, oxygen or sulfur.

Also included within the scope of this invention are the non-toxic pharmaceutically-acceptable acid addition salts of the compounds of our invention formed by reaction with such pharmaceutically-acceptable non-toxic acids as hydrochloric acid, hydrobromic acid, acetic acid, ascorbic acid, glutamic acid, lactic acid, tartaric acid, maleic acid, phosphoric acid, benzoic acid, and the like.

The compounds represented by the above formula are useful as antiarrhythmic agents and can be used to overcome cardiac irregularities. The compound of the present invention are formulated and utilized in the conventional manner as is well known in the antiarrhythmic art as shown by U.S. Pat. Nos. 3,084,156, 3,169,968, 3,133,929, 3,272,819, 3,332,951, 3,334,106, 3,350,403, 3,350,404, 3,401,170 and others.

The amine bases of this invention are high-boiling substances which crystallize slowly at ordinary room temperatures such as about 20°–30° C. The acid addition salts of such amine bases form readily by mixing the base with a stoichiometrically equivalent quantity of the selected acid in a relatively nonpolar solvent such as diethylether. The acid addition salts which are formed in this manner readily precipitate from solution as white crystalline solids.

The compounds of the present invention are prepared in accordance with processes set forth in the following flow sheet.

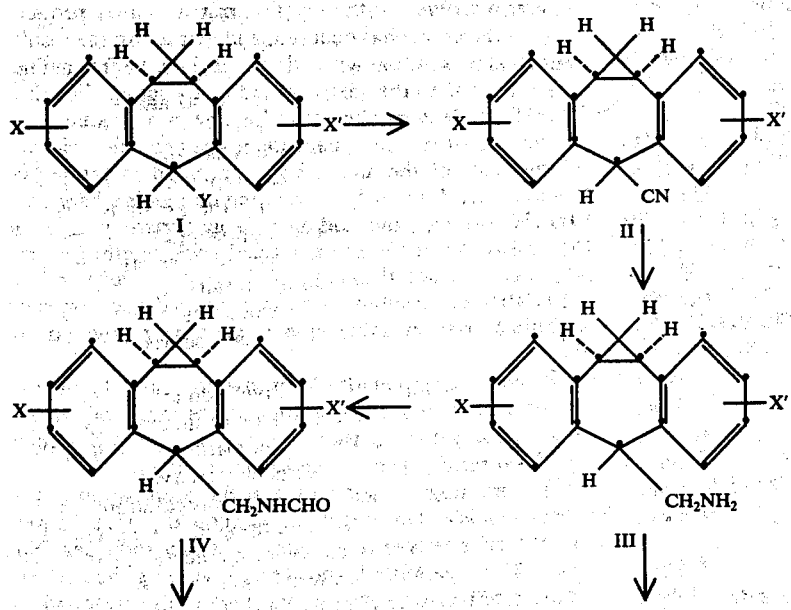

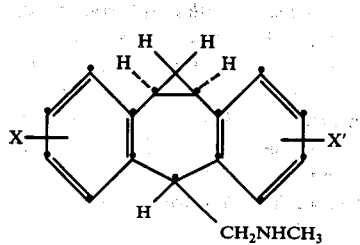

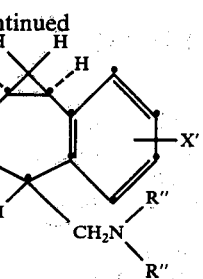

VII

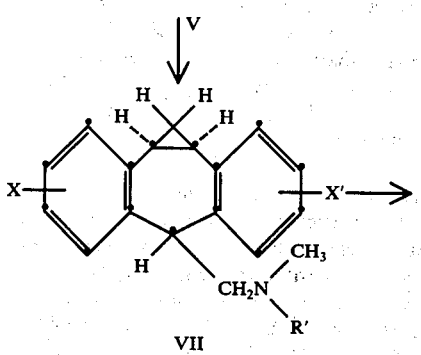

VII

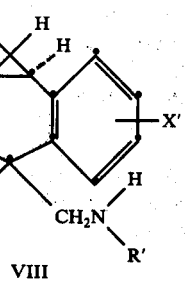

VIII wherein Y is halogen (preferably chlorine or bromine), X and X' are as previously defined and R' and R" are as previously defined.

The active compounds of this invention are represented by compounds III, V, VI, VII and VIII.

In accordance with our invention, compound I, wherein Y is a halogen, is reacted with a metal cyanide in a liquid diluent such as acetonitrile to replace the halo substituent and produce compound II, a 4-cyano-dibenzobicyclo[5.1.0]octane which is reduced with an alkali metal aluminum hydride to produce the corresponding 4-aminomethyl derivative, compound III.

The N-formyl compounds, IV, are produced by reaction of the amines, III, an alkyl formate. Although this reaction may be carried out in a solvent, a preferred method for effecting this reaction is by the use of excess alkyl formate. The N-formyl compounds, IV, are reduced with an alkali metal aluminum hydride to produce the corresponding 4-methylaminomethyl commpounds, V. The 4-methylaminomethyl compound represented by formula V may be converted to the corresponding N-alkyl-N-methyl tertiary amino compound, VI, by acylation followed by reduction. Thus the secondary amine, V, is acylated, for example, with acetic anhydride, propionic anhydride or butyric anhydride to form the corresponding amide which is then reduced to the tertiary amine using suitable reducing agent such as lithium aluminum hydride. Thus reaction of the N-methylamino compound, V, with acetic anhyride, propionic anhydride or butyric anhydride followed by reduction with lithium aluminum hydride gives, respectively, a compound having the formula, VI, wherein R is either ethyl, propyl or butyl. N-methy-N-alkylamines corresponding to formula VI may be converted to the corresponding monoalkylaminomethyl compounds of formula VIII by reaction of the N-alkyl-N-methyl compound with a halo formate or a halothioformate to produce the corresponding urethane or thiourethane intermediate. The urethane intermediate thus produced is then subjected to hydrolysis to produce the corresponding secondary amine. The hydrolysis is preferably carried our under basic conditions.

The 4-aminomethyl derivatives, III, are likewise converted by a process of acylation and reduction to produce the corresponding dialkylaminomethyl compounds represented by formula VII. Thus the primary amines of formula III are acylated, for example, with acetic anhydride, propionic anhydride or butyric anhydride to form the corresponding amide and the resulting amide reduced to the corresponding secondary amine using a suitable reducing agent such as lithium aluminum anhydride. The dialkylamines are obtained from the monoalkylamines by again acylating and then reducing the resulting amide. The preparation of these compounds of formula VII wherein the alkyl substituents attached to the nitrogen are different, can be readily achieved by appropriate selection of the acylating agent.

The primary, secondary and tertiary amino compounds of this invention, prepared as described above, are each isolated and purified by methods well known in the art for the isolation and purification of known nonvolatile amines. Such well known procedures involve hydrolysis of the reaction mixtures after production of the amine has occured, and extracting the resulting alkaline solution with ether to isolate the free amine; separating the ether extract; and evaporating the ether therefrom, leaving the desired amine as a residue.

The non-toxic pharmaceutically-acceptable acid addition salts of the amine bases prepared in the above manner are formed by dissolving the amine base in a suitable solvent and adding an appropriate amount of the desired acid. When a solvent such as ether is employed, in which the acid addition salts of these amines are relatively insoluble, the formed acid addition salts precipitate from solution and may be recovered by filtration.

The new compounds of our invention are obtained as a mixture of geometric isomers or as independent isomers. The geometric isomers which are isolated in their pure form may differ in biological activity.

The starting materials used in the preparation of the compounds of our invention, compound I, are prepared in accordance wth the process of application Ser. No. 662,881 of Englehardt and Remy involving the conversion of dibenzocyloheptenone into the corresponding 8,8-dihalo-2,3,5,6-dibenzobicyclo[5.1.0]-octane-4-one, reduction of said ketone with potassium borohydride into the corresponding 8,8-dihalo-2,3,5,6-dibenzobicyclo[5.1.0]octane-4-ol, treatment of said hydroxy compound with lithium and butanol to produce the corresponding 2,3,5,6-dibenzobicyclo[5.1.0]octane-4-ol and treating said 4-ol compound with dry hydrogen chloride to produce the corresponding 4-chloro-2,3,5,6-dibenzobicyclo[5.1.0]octane, the starting material of the present application.

EXAMPLE 1

4-Chloro-2,3,5,6-dibenzobicyclo[5.1.0]octane (I; X = X' = H, Y = Cl)

4-Hydroxy-2,3,5,6-dibenzobicyclo[5.1.0]octane (5.34 g., 0.024 mole) is dissolved in 380 ml. of benzene. The solution is cooled in an ice bath, stirred magnetically, and a stream of hydrogen chloride gas is bubbled into the solution for 10 minutes. Calcium chloride is added to the solution to absorb the water formed as a by-product. The mixture is allowed to stand overnight at room temperature. The calcium chloride is removed by filtration, and the benzene is removed by evaporation under reduced pressure from a water bath at 40° C. The residue, a viscous syrup, weighs 5.76 g.

EXAMPLE 2

4-Cyano-2,3,5,6-dibenzobicyclo[5.1.0]octane (II, X = X' = H)

Into a 1 liter 3-necked flash equipped with stirrer and reflux condenser with a calcium chloride drying tube, is placed 4-chloro-2,3,5,6-dibenzo-bicyclo[5.1.0]octane (21.53 g., 0.0893 mole), silver cyanide (14.90 g., 0.115 mole), and acetonitrile (750 ml.). The mixture is stirred and heated at reflux for 43 hours. The boiling mixture is filtered and the residue is washed with boiling acetonitrile. The acetonitrile is removed from the combined filtrate and washings by distillation under reduced pressure from a water bath at 80° C. There remains 20.0 g. of a clear yellow oil which was identified as 4-cyano-2,3,5,6-dibenzobicyclo[5.1.0]octane.

EXAMPLE 3

2,3,5,6-Dibenzobicyclo[5.1.0]octan-4-methylamine hydrochloride (III, X = X' = H)

A 2 liter 3-necked round bottom flask, equipped with dropping funnel stirrer, and condenser with calcium chloride drying tube, is flushed with nitrogen and flame dried. Into the flask is placed lithium aluminum hydride (5.46 g., 0.0144 mole) and ether (500 ml., dried over molecular sieves, Linde type 4A). The suspension is stirred and a solution of aluminum chloride (19.21 g., 0.144 mole) in ether (400 ml.) is added dropwise over a period of 40 minutes. When the addition is complete, the mixture is stirred for an additional ten minutes. A solution of 4-cyano-2,3,5,6-dibenzobicyclo[5.1.0]octane (20.0 g., 0.0865 mole) in ether (300 ml.) is added dropwise over 1.75 hours. A white granular precipitate is present at the end of the addition. The mixture is stirred at room temperature overnight. Water (25 ml.) and then sodium hydroxide (400 ml. of 5N. solution) is added to hydrolyze the mixture. The mixture is transferred to a separatory funnel and the ether is separated. The alkaline aqueous phase is extracted with ether (2 × 250 ml.). All the ether phases are combined, washed with water and dried over magnesium sulfate. The magnesium sulfate is removed by filtration and the ether is removed by distillation under reduced pressure. 2,3,5,6-Dibenzobicyclo[5.1.0]-octan-4-methylamine remains as a clear oil that crystallizes on standing.

The hydrochloride salt can be prepared by dissolving the amine III (X = X' = H) in ether and treating the solution with dry gaseous hydrogen chloride. A white crystalline hydrochloride salt precipitates. This material is filtered off and purified by recrystallization from isopropyl alcohol or by sublimation in vacuo to give 2,3,5,6-dibenzobicyclo[5.1.0]octan-4-methylamine hydrochloride, m.p. 297°–300° C. (dec.). Anal. Calc'd. for $C_{17}H_{17}N \cdot HCl$: C, 75.13; H, 6.67; Cl, 13.05. Found: C, 75.53; H, 6.68; Cl, 12.85.

EXAMPLE 4

N-Formyl-2,3,5,6-dibenzobicyclo[5.1.0]octan-4-methylamine (IV, X = X' = H)

A solution of 2.46 g. (0.0105 mole) of 2,3,5,6-dibenzobicyclo[5.1.0]octan-4-methylamine in 100 ml. of ethyl formate is heated under reflux for 24 hours. On cooling to room temperature, lustrous white plates separate from solution. The ethyl formate is removed by distillation and the residue is recrystallized from benzene to give N-formyl-2,3,5,6-dibenzobicyclo[5.1.0]-octan-4-methylamine, m.p. 180.5°–181.5° C.

Anal. Calc'd. for $C_{18}H_1NO$: C, 82.10; H, 6.51; N, 5.32. Found: C, 81.86; H, 6.24; N, 5.40.

EXAMPLE 5

N-Methyl-2,3,5,6-dibenzobicyclo[5.1.0]octan-4-methylamine hydrochloride (V, X = X' = H)

A 1 liter 3-necked round bottom flask, equipped with dropping funnel, stirrer, and condenser with calcium chloride drying tube, is flushed with nitrogen and flame dried. Into the flask is placed lithium aluminum hydride (0.424 g., 0.0112 mole) and ether (30 ml.). The suspension is stirred and a solution of 1.96 g. (0.00745 mole) of N-formyl-2,3,5,6-dibenzobicyclo[5.1.0]octan-4-methylamine in 800 ml. of dry ether is added dropwise over 75 minutes. The mixture is stirred for 24 hors at room temperature. Water (10 ml.) and then sodium hyroxide (25 ml. of a 40% solution) is added slowly to hydrlyze the mixture. The mixture is transferred to a separatory funnel, and the other is separated. The alkaline aqueous phase is extracted with ether (2 × 50 ml.). All the ether phases are combined and dried over magnesium sulfate. The magnesium sulfate is removed by filtration and the clear, colorless ether filtrate is treated with dry gaseous hydrogen chloride. A white crystalline hydrochloride salt precipitates. This material is filtered off and purified by recrystallization from an isopropyl alcohol-ether mixture to give N-methyl-2,3,5,6-dibenzobicyclo[5.1.0]octan-4-methylamine hydrochloride, m.p. Anal. Calc'd. for $C_{18}H_{19}N \cdot HCl$: C, 75.64; H, 7.05; Cl, 12.41. Found: C, 75.38; H, 6.77; Cl, 12.43.

What is claimed is:

1. A compound of the formula:

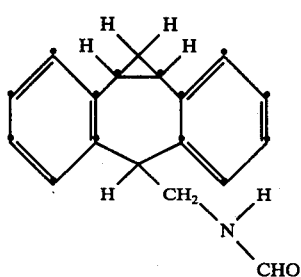
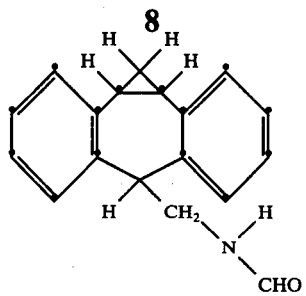
and the non-toxic pharmaceutically acceptable acid addition salts thereof.
2. N-Formyl-2,3,5,6-dibenzobicyclo[5.1.0]octan-4-methylamine.
* * * * *